(12) United States Patent
Siegel

(10) Patent No.: US 6,594,549 B2
(45) Date of Patent: Jul. 15, 2003

(54) WEB-ENABLED MEDICATION DISPENSER

(76) Inventor: Bruce Siegel, 720 S. Willow Ave., Tampa, FL (US) 33606

( * ) Notice: Subject to any disclaimer, the term of this patent is extended or adjusted under 35 U.S.C. 154(b) by 45 days.

(21) Appl. No.: 09/824,813

(22) Filed: Apr. 4, 2001

(65) Prior Publication Data
US 2002/0147526 A1 Oct. 10, 2002

(51) Int. Cl.⁷ .............................................. G06F 17/00
(52) U.S. Cl. ..................... 700/241; 700/237; 700/242; 700/243; 221/2; 221/3; 221/15
(58) Field of Search ................. 700/231, 232, 700/236, 241, 242, 243, 244, 237; 221/2, 3, 8, 15, 9, 10; 368/10

(56) References Cited

U.S. PATENT DOCUMENTS

| | | | | |
|---|---|---|---|---|
| 4,572,403 A | * | 2/1986 | Benaroya | 221/15 |
| 4,785,969 A | * | 11/1988 | McLaughlin | 221/15 |
| 5,014,875 A | * | 5/1991 | McLaughlin et al. | 221/122 |
| 5,176,285 A | * | 1/1993 | Shaw | 221/113 |
| 5,392,952 A | * | 2/1995 | Bowden | 221/15 |
| 5,564,593 A | * | 10/1996 | East, Sr. | 221/121 |
| 5,609,268 A | * | 3/1997 | Shaw | 221/2 |
| 5,852,590 A | * | 12/1998 | de la Huerga | 368/10 |
| 6,011,999 A | * | 1/2000 | Holmes | 312/215 |
| 6,163,736 A | * | 12/2000 | Halfacre | 221/102 |
| 6,219,587 B1 | * | 4/2001 | Ahlin et al. | 700/233 |
| 6,304,797 B1 | * | 10/2001 | Shusterman | 700/236 |
| 6,393,339 B1 | * | 5/2002 | Yeadon | 700/232 |
| 6,401,991 B1 | * | 6/2002 | Eannone | 221/103 |

* cited by examiner

Primary Examiner—Khoi H. Tran
(74) Attorney, Agent, or Firm—Peter A. Borsari (57) ABSTRACT

A medication dispensing system capable of connecting to the Internet is provided. The medication dispensing system can be in the form of a periphery device having electronic means for linkage to a personal computer, PDA, cell phone or WEB TV or can be a stand-alone, on-site terminal having means to connect to the Internet. The medication dispensing system comprises a rotatable medication tray having a plurality of compartments, a servo-mechanism operatively connected to the medication dispensing tray, a microprocessor based controller electronically connected to the servo-mechanism and being programmable to rotate the dispensing tray at a pre-set time. The controller also comprises a data store for maintaining and transmitting a variety of patient information, including the patient's medication regimen and compliance schedule. When connected to the Internet, the medication dispensing system transmits compliance and non-compliance notifications, allows the patient to order a refill medication or a new pre-filled dispensing tray, and provides the patient with healthcare news and databases.

26 Claims, 10 Drawing Sheets

WEB-ENABLED MEDICATION DISPENSER

FIELD OF INVENTION

The present invention relates to a medication dispensing system which is capable of connecting to the Internet. More particularly, the medication dispensing system can be in the form of a periphery device having electronic communications means for linkage to a personal computer, personal digital assistant (PDA), cell phone, WEB-TV, or combinations thereof, or may be in the form of a stand-alone on-site terminal having electronic communications means for connecting directly to the Internet. The web-enabled medication dispensing system of the present invention is designed to facilitate medication dispensing, monitoring compliance of a specified medication regimen and link the patient/user to one or more caregiver(s), pharmacies, physicians, pharmaceutical companies, medical supply companies and other medical businesses, healthcare and medical related databases and emergency personnel via the Internet.

BACKGROUND OF THE INVENTION

The prior art is replete with devices to hold and dispense medications. A simple such device commonly in use today is a plastic container divided into seven compartments, each compartment having a hinged lid and designated for a particular day of the week. The user places his daily medication requirement into each of the compartments and removes the medication from the designated daily compartment as desired. Another simple device is a container in the form of a disk which holds a month supply of a medication, such as a birth control pill which enables the user to remove the medication on a daily basis. Although simple to use, there are several drawbacks to such containers. For example, the container does not provide any means to alert the user that it is time to remove the medication nor does it offer any means to ensure a caregiver, physician or the like that the user is in compliance with the medication regimen.

More complicated dispensing systems have been developed in order to ensure compliance. For example, U.S. Pat. No. 5,710,551 to Ridgeway, issued Jan. 20, 1998, provides a self-medication monitoring system that assures compliance with prescribed dosage schedules through a telephone line communications link to a central monitoring system. U.S. Pat. No. 5,850,344 to Conkright, issued Dec. 15, 1998, discloses a computer-controlled medication dispensing and timing system that uses a modem communication between the dispenser and a commuter network. A significant drawback to these systems is that the user must be within a prescribed local network.

Similarly, U.S. Pat. No. 5,971,594 to Sahai et al., issued Oct. 26, 1999, is directed to an on-site medication dispensing system that monitors whether a patient has taken a medication by means of a central computer station and provides notification to a caregiver if the medication has not been taken. U.S. Pat. No. 5,993,046 to McGrady et al., issued Nov. 30, 1999, discloses a local area network controlled medication dispensing system. U.S. Pat. No. 4,695,954 to Rose et al., discloses a medication dispensing system including a portable memory device for controlling the dispenser and monitoring patient compliance.

Despite the varied medication dispensing systems commercially available today, a need still exists for a medication dispensing system which alerts the patient/user when it is time to take a medication and which is capable of accessing the Internet. Such a medication dispensing system should be simple and easy to use by the patient/user, provide proper dosing and timing of medication dispensing and offer the patient/user the option of obtaining a dispensing tray which has been pre-filled with the proper medication(s). Such a medication dispensing system also should be capable of being either a portable unit which can be transported by the patient and still be connectable to the Internet or as a stand-alone on site terminal. In addition, such a medication dispensing system should be programmable to the specific requirements of the patient and offer the patient a variety of compliance schedules. Moreover, such a medication dispensing system should connect the patient/user to a predetermined Internet Service Provider in order to access designated databases and web-sites relating to healthcare and to the user's specific medication regimen.

SUMMARY OF THE INVENTION

Accordingly, it is an object of the present invention to provide a medication dispensing system which is capable of accessing the Internet.

It also is an object of the present invention to provide a web-enabled medication dispensing system which alerts the patient/user when it is time to take a medication.

It is another object of the present invention to provide a web-enabled medication dispensing system which is simple and easy to use.

It is yet another object of the present invention to provide a web-enabled medication dispensing system which provides proper dosing of medication and proper timing of the dispensing of such medication.

It is still another object of the present invention to provide a web-enabled medication dispensing system which offers the patient/user with a medication dispensing tray which may be loaded by the patient/user or which may be pre-filled by a pharmacy, physician's office or medication supply house.

It is an additional object of the present invention to provide a web-enabled medication dispensing system which monitors a patient's compliance with his/her medication regimen and provides a variety of compliance schedules.

It is a further object of the present invention to provide a web-enabled medication dispensing system which is capable of being either a portable unit which can be transported by the patient/user and having electronic communications means for linkage to a personal computer, personal digital assistant (PDA), cell phone, WEB-TV, or combinations thereof, in order to connect to the Internet.

It is yet a further object of the present invention to provide a web-enabled medication dispensing system which is in the form of a stand-alone on-site terminal capable of connecting to the Internet.

It is still a further object of the present invention to provide a web-enabled medication dispensing system which is programmable to the specific requirements and medication regimen of the patient.

It is an additional object of the present invention to provide a web-enabled medication dispensing system which is connectable to the Internet or an Internet Service Provider and which can transmits Compliance Notifications to a predetermined caregiver or other dedicated receiver, thereby monitoring compliance.

It also is an object of the present invention to provide a web-enabled medication dispensing system which is connectable to the Internet or an Internet Service Provider and which can transmit a Non-Compliance Notification to a predetermined caregiver or other dedicated receiver when medication has not been dispensed.

It is another object of the present invention to provide a web-enabled medication dispensing system which connects the patient/user to the Internet or an Internet Service Provider in order to provide the patient/user with automatic on-line re-ordering of medication.

It is yet another object of the present invention to provide a web-enabled medication dispensing system which connects the patient/user to the Internet or an Internet Service Provider in order to provide the patient/user with on-line access to his/her pharmacy and/or physician.

It is still another object of the present invention to provide a web-enabled medication dispensing system which connects the patient/user to the Internet or an Internet Service Provider in order to provide the patient/user with on-line access to medical and healthcare databases and web-sites.

It is another object of the present invention to provide a web-enabled medication dispensing system which connects the patient/user to the Internet or an Internet Service Provider in order to provide the patient/user with medical, healthcare and/or drug marketing information.

It is an additional object of the present invention to provide a web-enabled medication dispensing system which provides an Emergency Notification to emergency authorities.

Additional objects, advantages and novel features of the invention will be set forth in part, in the description and claims which follow, and in part will become apparent to those skilled in the art upon examination of the following specification and claims or which may be learned by practice of the invention.

These and other objects of the present invention are accomplished by providing a medication dispensing system comprising a base housing, a rotatable medication dispensing tray removably disposed with the base housing and having a plurality of compartments, each of which is capable of retaining at least one medication, a servo-mechanism operatively connected to the rotatably medication dispensing tray, a microprocessor based controller electronically connected to the servo mechanism and being programmable to rotate the dispensing tray at a pre-set time and an electronic communication means capable of establishing access to the Internet. In one embodiment, the medication dispensing system is a portable device wherein the electronic communication means is a parallel or serial port or USB slot connectable to a computer, personal digital assistant, cell phone, WEB-TV or combinations thereof. In another embodiment, the medication dispensing system is a stand alone device having a display screen wherein the electronic communication means is a wire communication device (e.g. modem) or wireless communication device.

BRIEF DESCRIPTION OF THE DRAWINGS

The present invention will be better understood with reference to the appended drawing sheets, wherein.

DETAILED DESCRIPTION

Figure 1A:
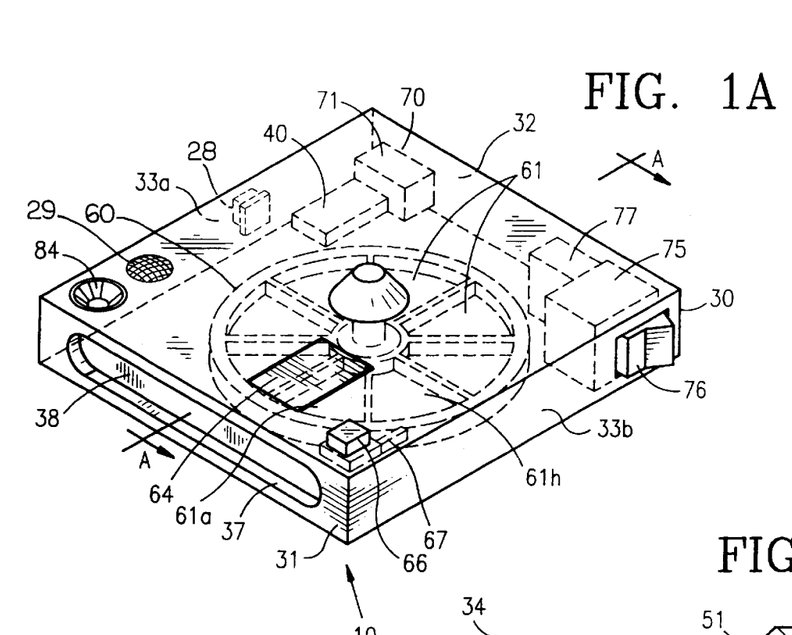
FIG. 1A is a cutaway top perspective view of the web-enabled medication dispensing system of the present invention having a front panel for loading a medication dispensing tray.
Figure 1B:
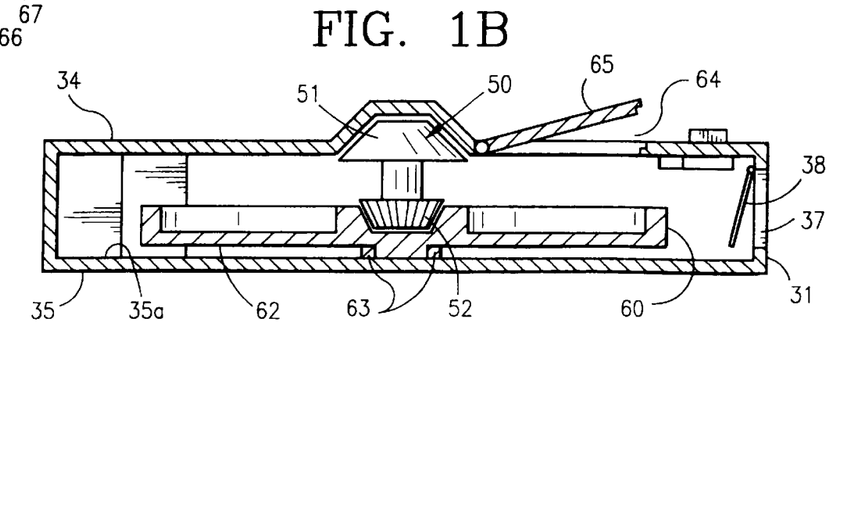
FIG. 1B is side view of the web-enabled medication dispensing system illustrated in FIG. 1A taking along the line A—A.

The present invention relates to web-enabled medication dispensing system 10 which in one embodiment comprises a base housing, a rotatable medication dispensing tray disposed within said base housing, a servo-mechanism operatively connected to said medication dispensing tray, a microprocessor based controller, and an electronic communication means capable of providing a linkage to Internet. Referring to FIGS. 1A and 1B, the web-enabled medication dispensing system 10 comprises a base housing 30 having a front panel 31, a rear panel 32, side panels 33a and 33b which connect said front panel and said rear panel, a top panel 34 and a bottom panel 35, bottom panel 35 having an interior floor 35a. Disposed within the base housing 30 is a microprocessor controller 40, a servo mechanism 50 and a removable medication dispensing tray 60. The microprocessor controller 40 is electronically coupled to a servo mechanism 50 which in turn is operatively connected to a medication dispensing tray 60. The controller 40 may be any suitable microprocessor-based controller capable of electronic communication with the servo mechanism 50 and also capable of receiving, storing and implementing a medication dispensing program. Preferably, the controller 40 is provided with a servo drive interface for actuating the servo mechanism in order to rotate the medication dispensing tray 60.

The servo mechanism 50 comprises a servo motor 51 which cooperatively engages the medical dispensing tray 60 (hereinafter sometimes referred to as the dispensing tray) by means of a servo motor drive sprocket 52. The dispensing tray 60 preferably is in the form of a disk which is divided into a plurality of compartments 61. Referring to FIG. 1A, the medication dispensing tray is divided into a plurality of eight (8) compartments 61a to 61h, with compartment 61a being denoted the first or start compartment and compartment 61h being denoted the final or end compartment. Each compartment 61 is capable of storing a medication dosage. The underside 62 of the dispensing tray 60 is provided with a pivot and bushing assembly 63 which contacts and rests on the floor 35a of the bottom panel 35. The pivot and bushing assembly 63 enable the dispensing tray 60 to be rotated about the servo motor drive sprocket 52.

In the embodiment shown in FIGS. 1A and 1B, the dispensing tray 60 is introduced into the housing 30 through opening 37 disposed within front panel 31. Opening 37 can be of any suitable shape and must be of sufficient size to enable the dispensing tray 60 to be introduced into the base housing and removed therefrom. Preferably, opening 37 is in the form of an elongated slot. A closure 38, such as a swingable gate or hinged door, may be mounted to the front panel 31 in order to cover the opening 37 when it is not being used.

An access opening 64 is disposed within top panel 34 of the base housing 30, the access opening 64 being in communication with one of the plurality of compartments 61 of the medication dispensing tray 61 located within the base housing. In the initial setting, start compartment 61a lies under access opening 64, as shown for example, in FIG. 1A. A door or similar closure 65 is secured to the top panel 34, the door being of sufficient size that it lies completely over the access opening 64. The door 65 optionally can be provided with locking means, thereby preventing unauthorized access to the access opening 64. An internal speaker 84 also can be provided within the base housing 30, for example, mounted to the underside of top panel 34.

Figure 5A:
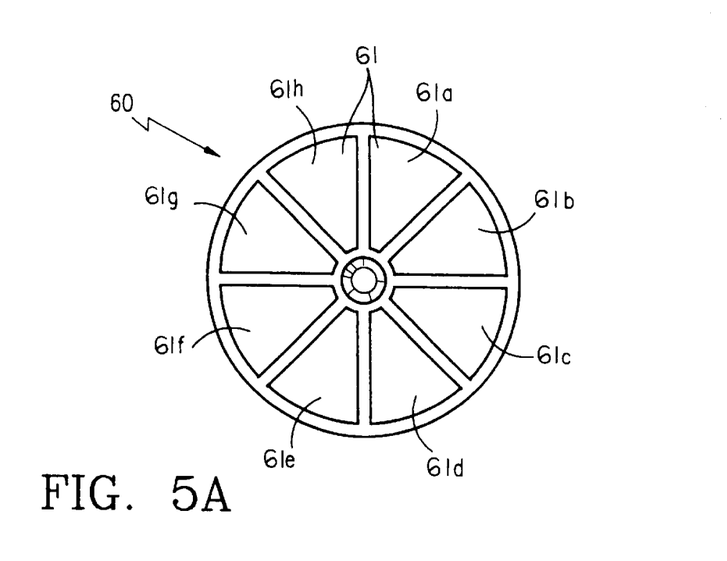
FIG. 5A is a top view of the medication dispensing tray of the present invention.
Figure 5B:
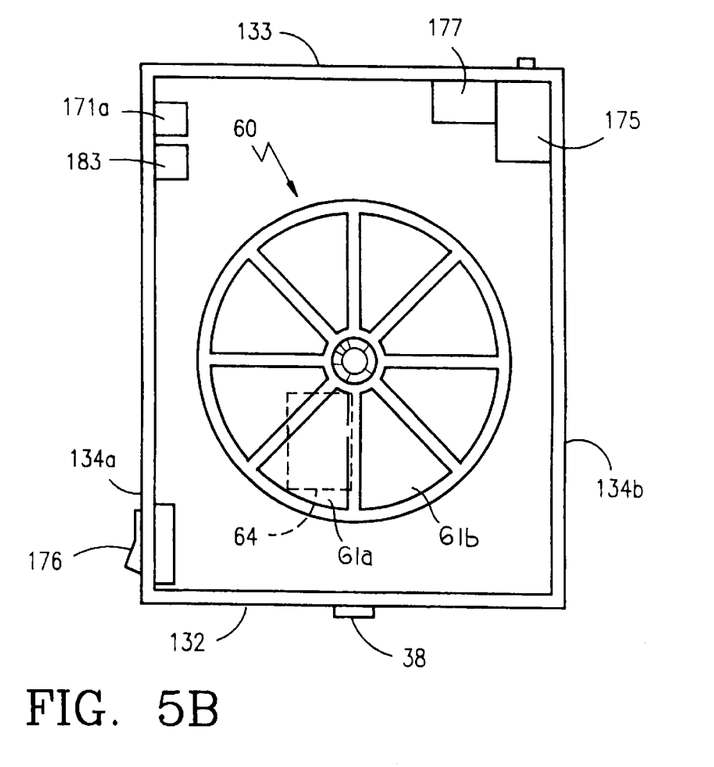
FIG. 5B is a cut-away top view of the web-enabled medication dispensing system of the present invention showing a compartment of medication dispensing tray.

Referring to FIGS. 5A and 5B, the medication dispensing tray 60 is rotated about the servo motor drive socket 52 by means of the servo motor 51. The servo motor 51 is configured to rotate the dispensing tray 60 in a counter-clockwise direction in such a manner that one compartment at a time is advanced. Thus, when the dispensing tray 60 is first introduced into the base housing 30 such that start compartment 61a lies beneath access opening 64, actuation of the servo mechanism will rotate the medication dispensing tray 60 by one compartment, thereby advancing compartment 61b to lie beneath the access opening 64. In an alternative embodiment, the base housing 30 may be provided with a spring activated mechanism such that the medication dispensing tray can be ejected from the base housing when it is desired to remove the tray.

Figures 2A, 2B:
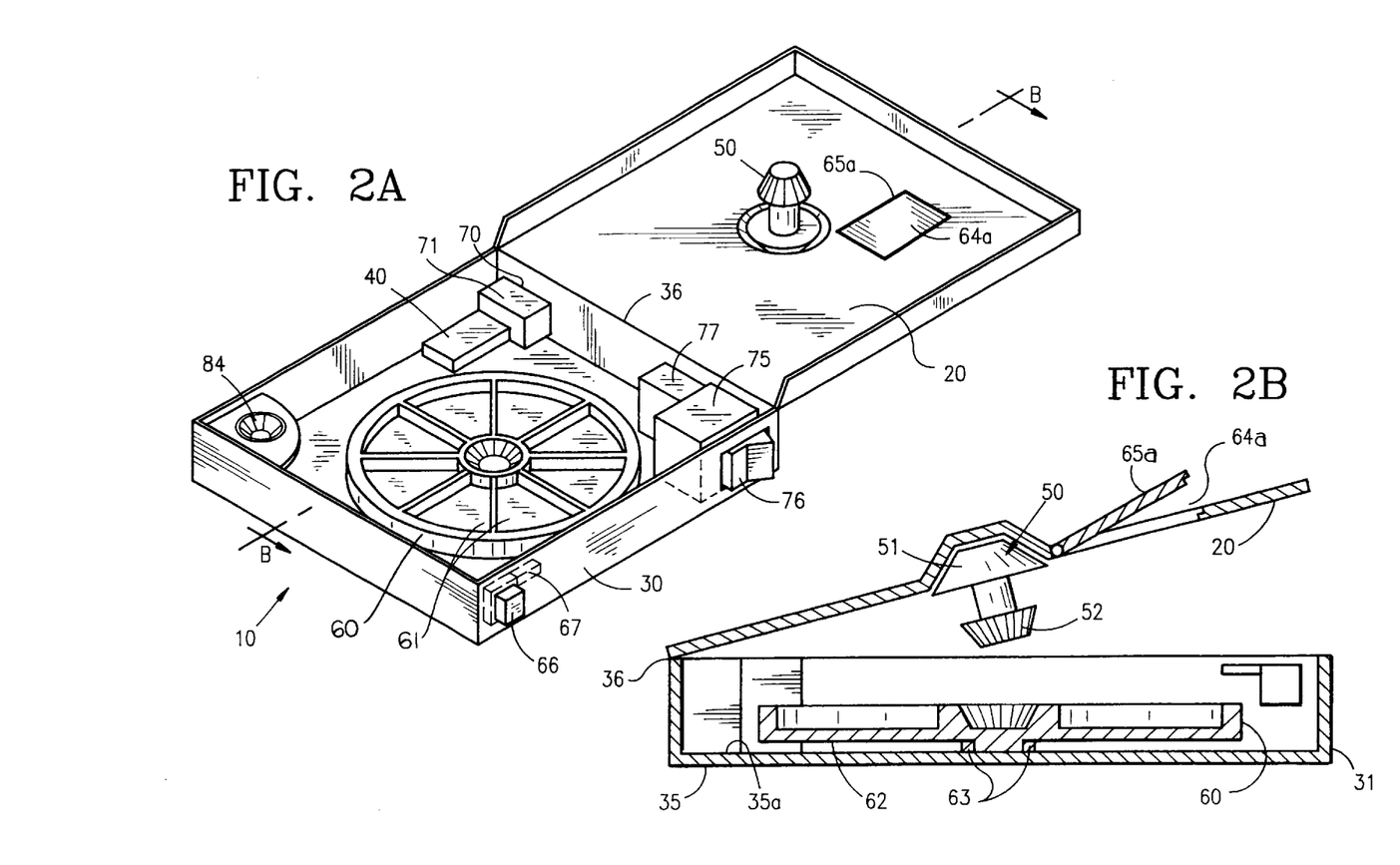
FIG. 2A is a top perspective view of the web-enabled medication dispensing system of the present invention having a top cover for loading a medication dispensing tray.
FIG. 2B is a is side view of the web-enabled medication dispensing system illustrated in FIG. 2A taking along the line A—A.

In a second embodiment, the web-enabled medication dispensing system of the present invention further comprises a top cover 20 hingedly connected to the base housing 30 as shown in FIGS. 2A and 2B. The top cover can be hingedly connected to the base housing by any suitable means known in the art, including for example, one or more hinge elements 36. In this embodiment, the top cover 20 is provided with an access opening 64a which is in communication with one of the plurality of compartments 61, and a door or similar closure 65a secured to the top cover 20 and covering access opening 64a. In this embodiment, the medication dispensing tray 60 is introduced into the base housing 30 simply by opening top cover 20 and inserting the tray into the base housing such that it rests on floor 35a.

The web-enabled medication dispensing system 10 further comprises an electronic communication means 70 capable of linking the medication dispensing system 10 to the Internet and a power supply 75. The electronic communication means 70 may be in the form of parallel or serial port or USB slot 71, capable of electronically connecting the medication dispensing system 10 to an Internet-ready device, such as a computer, PDA, cell phone, WEB-TV or combinations thereof. In this manner, the web-enabled medication dispensing system can be regarded as a computer periphery device. Power supply system 75 includes a standard AC/DC adaptor and associated on/off switch 76. Preferably, the power supply system also includes a battery back-up 77. In these two embodiments, the medication dispensing system 10 may be referred to sometimes hereinafter as the Internet-accessible medication dispensing system.

In a third embodiment, the web-enabled medication dispensing system of the present invention is in the form of a stand-alone on-site terminal. More particularly, as shown in FIGS. 3A, 3B, 4A, 4B and 4C, the web-enabled medication dispensing system 100 comprises a top housing 110 having a display screen 120 secured thereto which is electronically connected to a base housing 130. Disposed within the base housing 130 is the microprocessor-based controller 40, the servo mechanism 50 and the medication dispensing tray 60, as described hereinabove. Optionally, the microprocessor-based controller may be disposed in the top housing 110 as shown at 140.

Figure 3A:
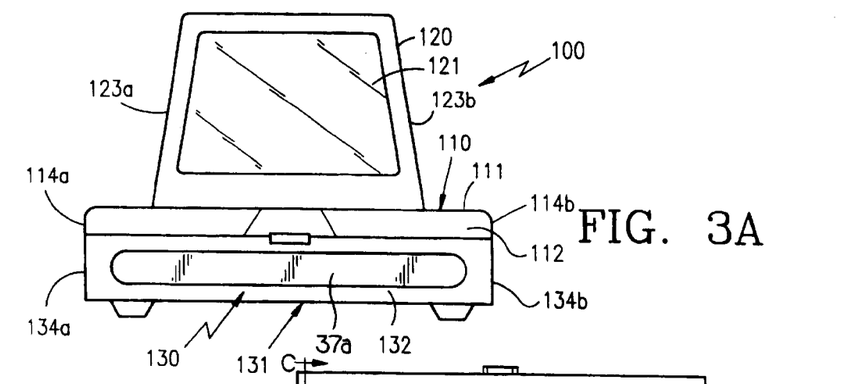
FIG. 3A is a front perspective view of the web-enabled medication dispensing system of the present invention.
Figure 3B:
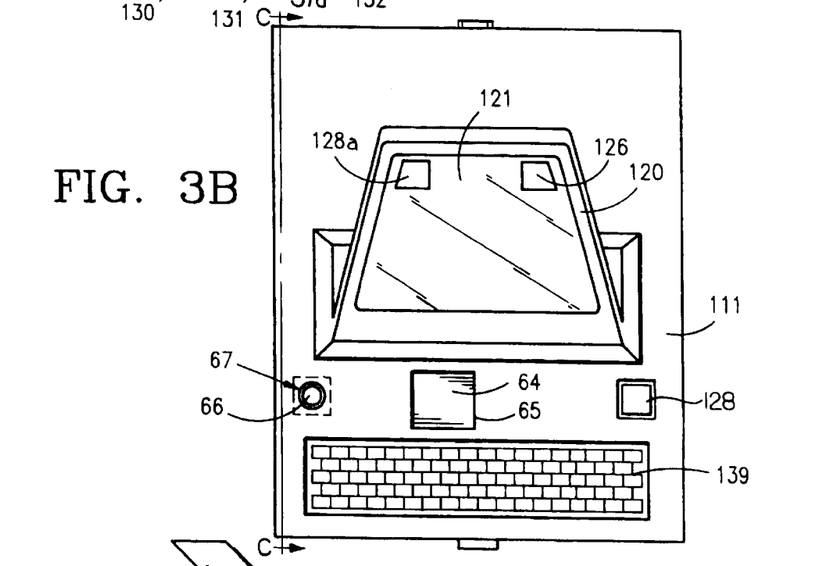
FIG. 3B is a top perspective view of the web-enabled medication dispensing system of the present invention.
Figure 4A:
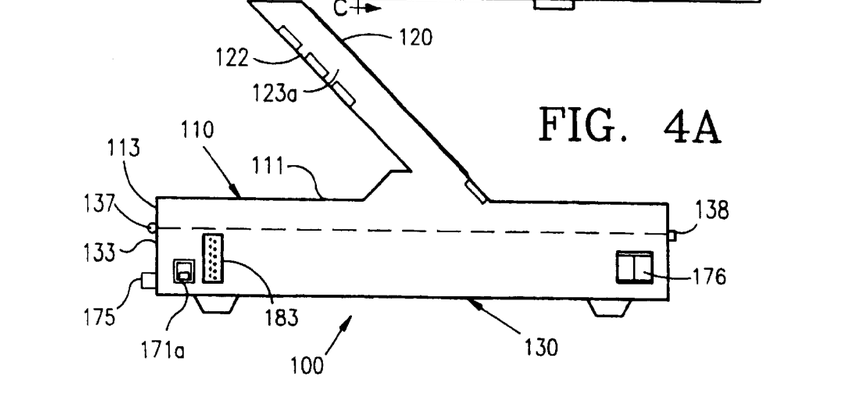
FIG. 4A is a side view of the web-enabled medication dispensing system of the present invention.
Figure 4B:
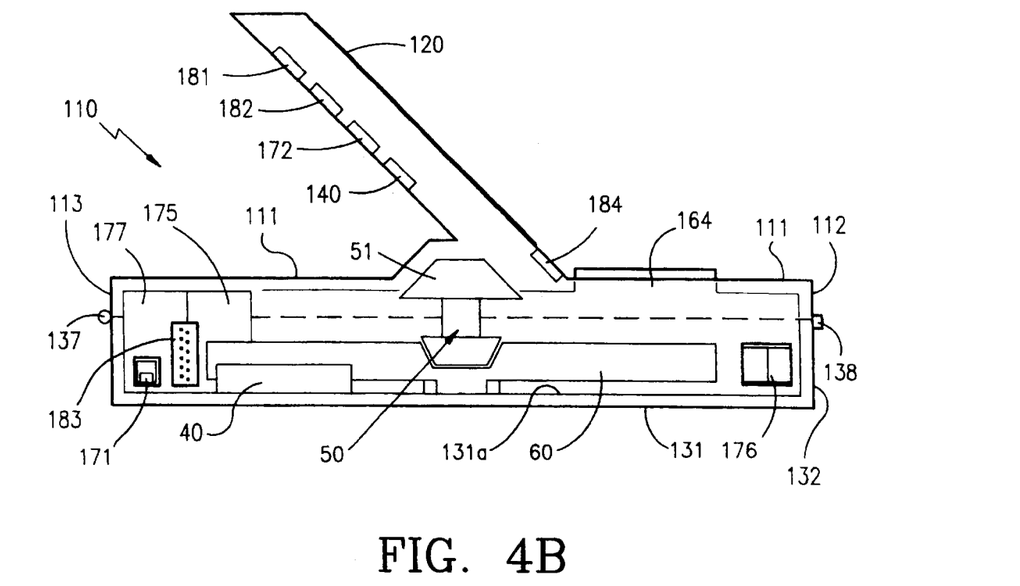
FIG. 4B is a side view of the web-enabled medication dispensing system of the present invention taken along line C—C.
Figure 4C:
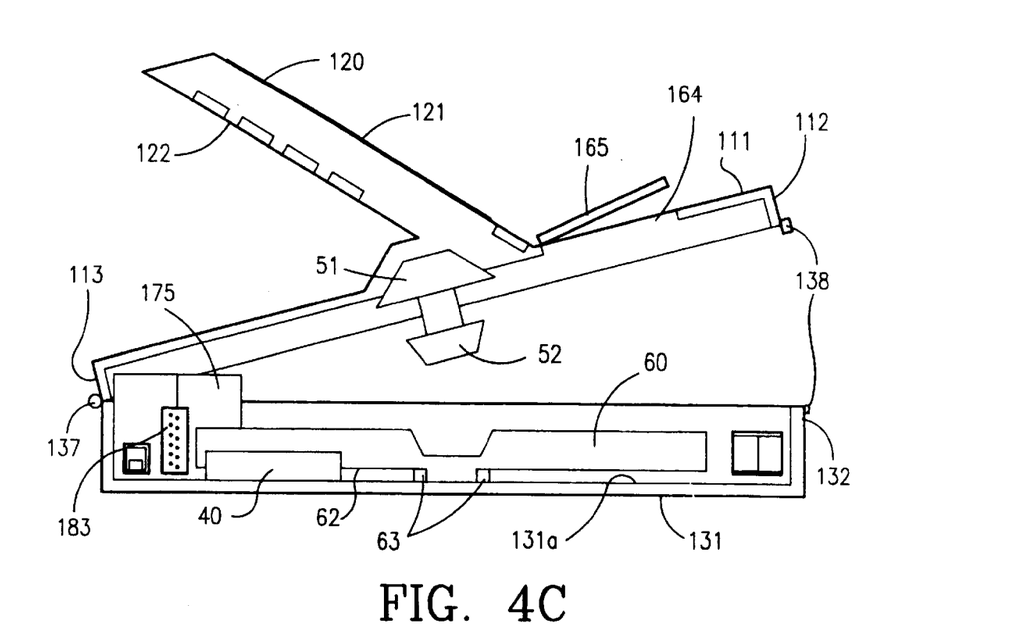
FIG. 4C is a partially exploded side view of the web-enabled medication dispensing system of the present invention taken along line C—C.

The top housing 110 either may be permanently secured to the base housing as shown in FIG. 3A or may be hingedly connected to the base housing 130 as shown in FIGS. 4B and 4C. Top housing 110 comprises a top panel 111, a front panel 112, a rear panel 113 and side panels 114 joining said front and rear panels 112 and 113. The base housing 130 comprises a bottom panel 131 having a floor 131a, a front panel 132, rear panel 133 and side panels 134a and 134b joining said front and rear panels 132 and 133. When the top housing 110 is permanently secured to the base housing 130, an opening 37a is provided in front panel 112, the opening 37a being of any suitable shape and of sufficient size to enable the dispensing tray 60 to be introduced into the base housing. Preferably, opening 37a is in the form of an elongated slot. A closure, such as a swingable gate or hinged door, may be mounted to the front panel in order to cover the opening when it is not in use.

Referring to FIGS. 4A, 4B and 4C, top housing 110 is hingedly connected to base housing 130 by any suitable means, including for example, one or more hinge elements 137 joining rear panel 113 to rear panel 133, thereby enabling the top housing 110 to be opened upwardly and away from the base housing 130. Front panels 112 and 132 can be provided with a cooperating latching mechanism 138, thereby enabling the top housing 110 to be detachably secured to the base housing 130. Optionally, the top panel 111 may be configured with a keyboard 119 or a touch-activated keyboard 129 may be incorporated into display screen 120. Top housing 110 is provided with an access opening 164 which is in communication with one of the plurality of compartments 61, and a door or similar closure 165 secured to the top housing 110 and covering access opening 164.

Display screen 120 can be any conventional display screen typically used with computers, such as an LCD display screen. Preferably, the display screen 120 is a touch-activated display screen. Display screen 120 comprises a front face 121, a rear face 122 and left and right side faces 123a and 123b. The display screen 120 is electronically connected to base housing 130 by any suitable means which will be well known to practitioners of the art.

The web-enabled medication dispensing system 100 further comprises electronic communication means 170 for connecting to the Internet and a power supply system 175. The communication means 170 may be in the form of a wire communication device 171, such as a modem and its associated connection jack 171a, or it may be in the form of a wireless communication device 172. Power supply system 175 includes a standard AC/DC adaptor and associates on/off switch 176. Preferably, the power supply system also includes a battery back-up 177. In this embodiment, the web-enabled medication dispensing system 100 may sometimes be referred to hereinafter as the Internet-ready medication dispensing system.

The medication dispensing system 100 also may comprise other conventional computer hardware, including for example, extended memory chip 181 (e.g. RAM) and its associated slot 182, a printer cable communications port 183, internal audio speaker 184, as well as an electronic connection means such as a parallel or serial port or USB slot for linking to a computer, personal digital assistant, cell phone, WEB TV and combinations thereof, and other conventional computer hardware, including for example, a sound card and a video card.

As shown for example in FIGS. 1A, 2A and 5, the medication dispensing tray 60 is divided into a plurality of compartments 61. The dispensing tray 60 can be divided into any suitable number of compartments in order to accommodate a variety of daily medication regimes and individual requirements. For example, the dispensing tray 60 can be provided with thirty-two (32) compartments in order to offer a one-month (e.g. thirty-one days) supply of medication for a patient who requires medication once a day. However, it is to be understood that the dispensing tray 60 can be designed with a different number of compartments in order to offer a week (seven day) supply or to accommodate a daily medication regimen in which a patient is required to take several medications over the course of a twenty-four hour period. Thus, for a medication regimen requiring four daily dispensings, the dispensing tray 60 can be provided with twenty-eight (28) compartments, thereby offering a week supply to the patient. Solely for the purposes of illustration, the medication dispensing tray 60 shown in FIG. 5A has eight (8) compartments 61a through 61h, compartment 61a being the start compartment and compartment 61h being the final compartment. Such a dispensing tray can accommodate a patient having a single daily medication requirement over a week (seven-day) period. Optionally, the medication dispensing tray can be provided with a non-rotatable top cover having an opening corresponding in size to one of the compartments 61. The medication dispensing tray also may be in the form of a rotatable cartridge which has been pre-loaded with the medication.

Figure 6:
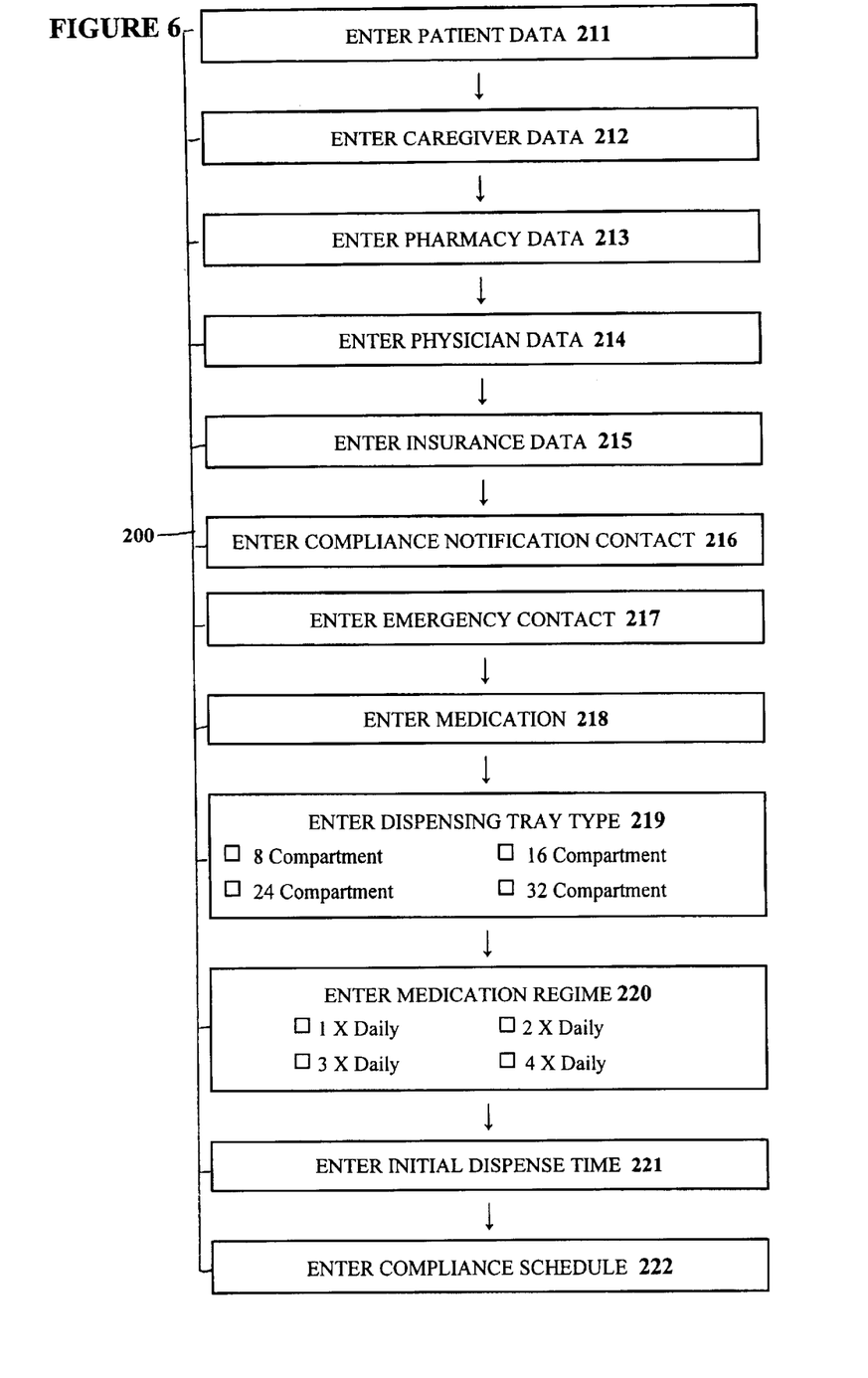
FIG. 6 is a flow chart illustrating the data entry program of the web-enabled medication dispensing system of the present invention.

As noted above, the web-enabled medication dispensing system of the present invention is provided with a medication dispensing program stored within controller 40. medication dispensing program can be either a pre-loaded program permanently stored in the controller 40 or can be downloadable program loaded to the controller by the user. It is to be understood that the term "user" may refer to the patient, that is the individual receiving the medication, or can be a caregiver, a pharmacist, physician, physician assistant, or the like. The medication dispensing program (hereinafter sometimes referred to as "Program") will enable a variety of data relating to the patient and the patient's medication regimen to be entered. Initial data entry can be created prior to first use or upon connection to the Internet. As illustrated in FIG. 6, suitable data entry 200 includes, for example, patient information 211 (name, address and phone number), caregiver information 212, pharmacy information 213, physician information 214, insurance information 215, compliance notification contact information 216, emergency contact information 217, medication names 218, and the like. The Program also will enable the user to input the type 219 of medication dispensing tray being used, the desired medication regimen 220 including the dispensing time 221 and the compliance schedule 222. For example, if the medication regimen is a once-daily medication regimen and if the medication dispensing tray 60 has thirty two compartments, the user enters a once-daily dispense of medication, the time the medication should be dispensed, and the type of dispensing tray (thirty two compartment). The Program then is set for dispensing medication once a day for a month (thirty-one day) period. As the controller 40 is in electronic communication with the servo mechanism 50, the controller will electronically actuate the servo mechanism 50 at the pre-set dispense time in order to advance a compartment 61 once a day.

Once the relevant patient information and selected medication regimen has been entered into the Program, each compartment 61 of the medication dispensing tray 60 is filled with the appropriate medication. The dispensing tray 60 can be filled by the patient/user prior to introducing the dispensing tray into the base housing. However, it is contemplated to be within the scope of this invention to provide a dispensing tray which has been pre-filled and forwarded to the patient/user and which can be disposed after use. For example, the dispensing tray can be pre-filled by the patient's pharmacy or physician's medical office, a medical supplier, a mail order pharmacy or the like. The disposable dispensing tray enables the patient/user to order a new pre-filled tray and simply dispose of the used tray.

In one embodiment, start compartment 61a is left empty. The user introduces the medication dispensing tray 60 into the base housing 30 such that start compartment 61a lies beneath the access opening 64 (64a or 164) in the second and third embodiments respectively). In the second and third embodiments, the top cover/top housing is closed upon the base housing and the latching mechanism is locked. The medication dispensing system now is set for dispensing, based on the parameters inputted for the medication regime.

In operation, when the pre-set time for dispensing has arrived, the controller 40 will actuate electronically the servo mechanism 50 which, in turn, will advance one compartment, for example compartment 61b, of the dispensing tray 60 such that the advanced compartment lies beneath the opening 64. The controller also will transmit a signal indicating that it is time to remove the medication from the compartment. The signal may be an audible signal through speaker 84/184, or may be a visual signal, such as a message flashing on the display screen 121 or may be a combination audio and visual signal. The patient/user responds to the visual and/or audio signal by depressing response button 66/166 disposed on the top panel. Response button 66/166 is in electronic communication with a microswitch 67/167. Actuation of the microswitch alerts the controller that the patient/user has received the signal and has removed the medication from the compartment. The controller 40 then is re-set to rotate the dispensing tray at the next pre-set time. In an alternate embodiment, actuation of the microswitch also unlocks door 65/165, thereby enabling the user to remove the medication from the compartment 61b.

In an alternate embodiment of the medication dispensing system, the controller 40 transmits an audio and/or visual signal to the patient/user indicating it is time to remove the medication from the compartment. The depression of response button 66/166 actuates the microswitch 67/167 which in turn actuates the servo mechanism 50 in order to advance one compartment of the dispensing tray. The user then opens the door and removes the medication. Actuation of the microswitch also alerts the controller that the medication has been removed from the dispensing tray. In this embodiment, the patient is able to manually override the medication dispensing system by depressing response button 66/166. The manual override allows the patient/user the option to remove medication from the dispensing tray at a time other than the pre-set dispense time.

In another alternative embodiment, actuation of the microswitch 167 can be achieved by use of a touch button on the touch-activated display screen 121. In this embodiment, the visual signal sent by controller 40 appears as a response touch button 126 on the display screen. Touching the response touch button actuates the microswitch as described above.

One feature of the web-enabled medication dispensing system of the present invention is the capability of accessing a predetermined Internet Service Provider (ISP) in order to gain access to designated databases and sites provided by the Internet Service Provider relating to health care and the user's medication regime, including for example, the user's pharmacy, searchable databases relating to drugs and diseases, businesses offering medical and health care items, and the like. The system also will enable the user to receive important medical news and healthcare update notices. The ISP may be a current on-line provider, a physicians group, a hospital group, a pharmacy, a pharmaceutical company, a medical supply house or any other entity capable of providing access to the Internet.

Access to the ISP will be dependent upon the type of medication dispensing system being used. As discussed above, for the Internet-accessible embodiments, linkage to an Internet accessible device, such as a computer, personal digital assistant or WEB-TV, is necessary for connection to the Internet Server. In the Internet-ready medication dispensing system 100, access to the Internet is available instantly. Upon first use, the controller 40 transmits the data initially entered into the medication dispensing program by the user to the Internet Server, thereby registering the patient. The first use may be prior to the initial dispensing of medication, immediately after the initial dispense, or at some time thereafter. Once registered, the user is provided with access to the Internet Server and particularly with access to medical databases and services noted above.

Another feature of the web-enabled medication dispensing system of the present invention is monitoring the patient's removal of the medication in order to determine that the patient is complying with the medication regime. The medication dispensing program includes a compliance schedule which the patient/user enters as part of the initial data entry described above. Compliance is monitored through the Internet Service Provider. The compliance schedule offers numerous options in order to accommodate the patient's requirements. Compliance options include, for example, strict compliance, daily compliance, weekly compliance and voluntary compliance, as discussed below. As compliance is monitored via the Internet, the compliance schedule is partially dependent on whether the medication dispensing system is Internet-accessible or Internet-ready.

Once the web-enabled medication dispensing system of the present invention has Internet access through electronic communication means 70/170, monitoring compliance is executed by the controller. More specifically, once the controller 40/140 has been alerted that the patient/user has removed the medication from the compartment, the controller will determine whether the selected compliance schedule instructs it to activate an automatic log-on to the ISP and transmit a Compliance Notification. If the selected compliance schedule is a strict compliance schedule, the controller will be instructed to activate an automatic log-on and transmit a Compliance Notification every time the controller is alerted that the patient/user has removed the medication from the compartment. If the selected compliance schedule is daily or weekly compliance schedule, the controller will be instructed to activate an automatic log-on and transmit a Compliance Notification at a pre-set time. If the selected compliance schedule is a voluntary compliance, the controller will be instructed not to log-on to the Internet until instructed by the user. The medication dispensing program also will enable the patient/user to manually log onto the ISP and query the patient/user as to whether a Compliance Notification should be transmitted. The Compliance Notification will report the time(s) that medication was removed medication dispensing tray compartment(s), thereby establishing the patient's compliance with the medication regimen and also monitoring whether the patient is removing the medication at the pre-set time, or at an earlier or later time.

Figure 7A:
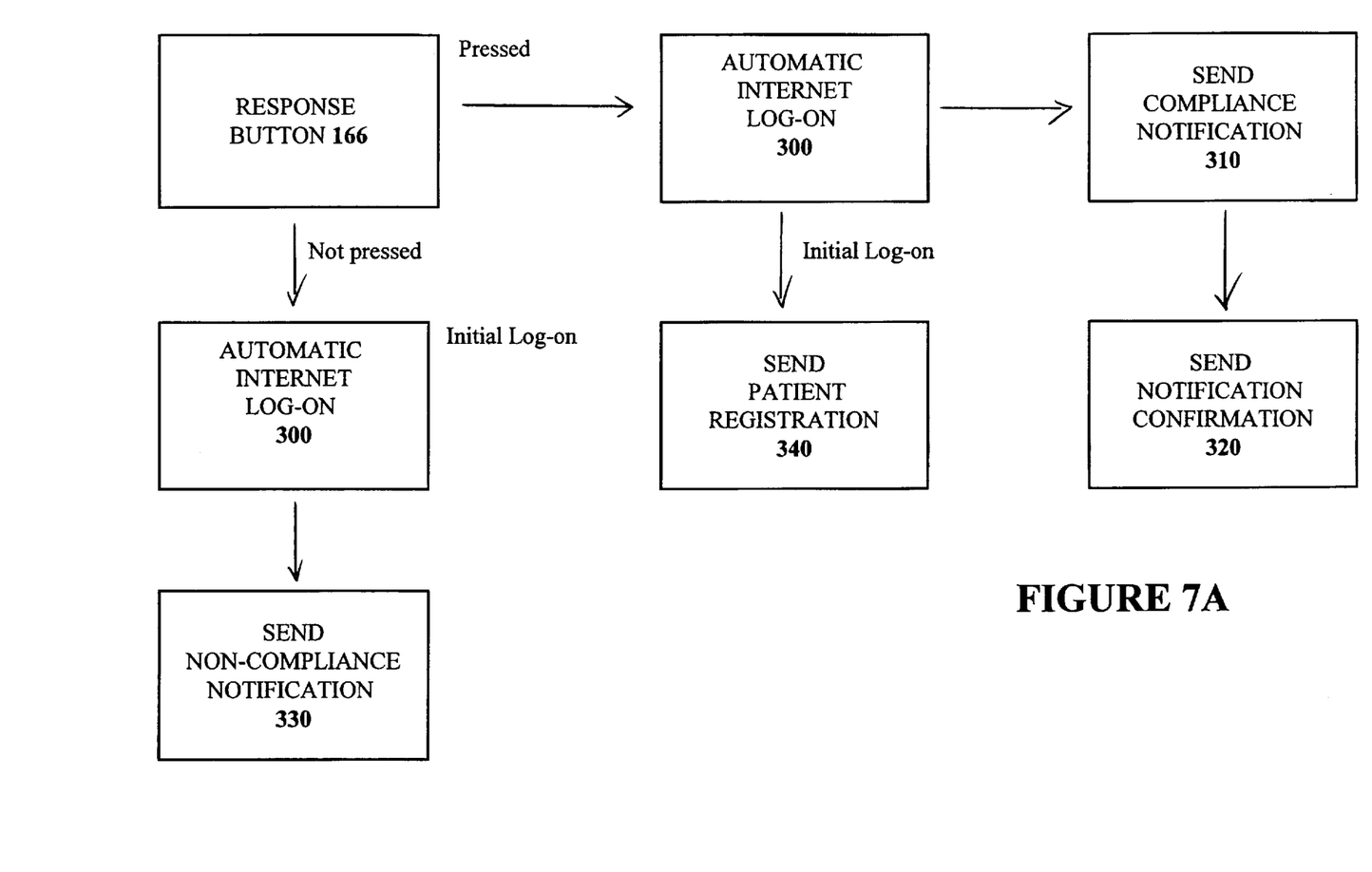
FIG. 7A is an operational flow chart illustrating one embodiment of a compliance feature of the web-enabled medication dispensing system of the present invention.

FIG. 7A shows an operational flow chart for a user utilizing the medication dispensing system 100 and having selected a strict compliance schedule. When the patient/user depresses response button 166 (or touch button 126), thereby alerting the medication has been removed from the compartment, the controller is instructed to transmit a Compliance Notification 310 reporting that the user is in compliance. The Compliance Notification 310 can be transmitted to the ISP, or to a caregiver, pharmacy, physician or any other receiver whom the user has designated in the Program as the receiver of the Compliance Notification. The Compliance Notification 310 can be in the form of an e-mail message, automated telephone call or other suitable means. Optionally, once the Compliance Notification has been sent, a Notification Confirmation 320 can be displayed on the display screen 121 to advise the user that the Notification was successfully transmitted.

If the patient/user does not depress response button 166 (or touch button 126) within a predetermined time frame, thereby alerting the controller 40/140 that the user has removed the medication from the compartment, the web-enabled medication dispensing system 100 will send a Non-Compliance Notification 330 to the designated receiver reporting that the user is not in compliance with the medication regime. The designated receiver then can contact the patient/user to determine why the patient is not in compliance with the medication regime. If the patient/user has not sent a prior registration to the ISP, that is, if the automatic log-on 300 is an initial log-on, the controller also will transmit the Patient Registration 340.

Figure 7B:
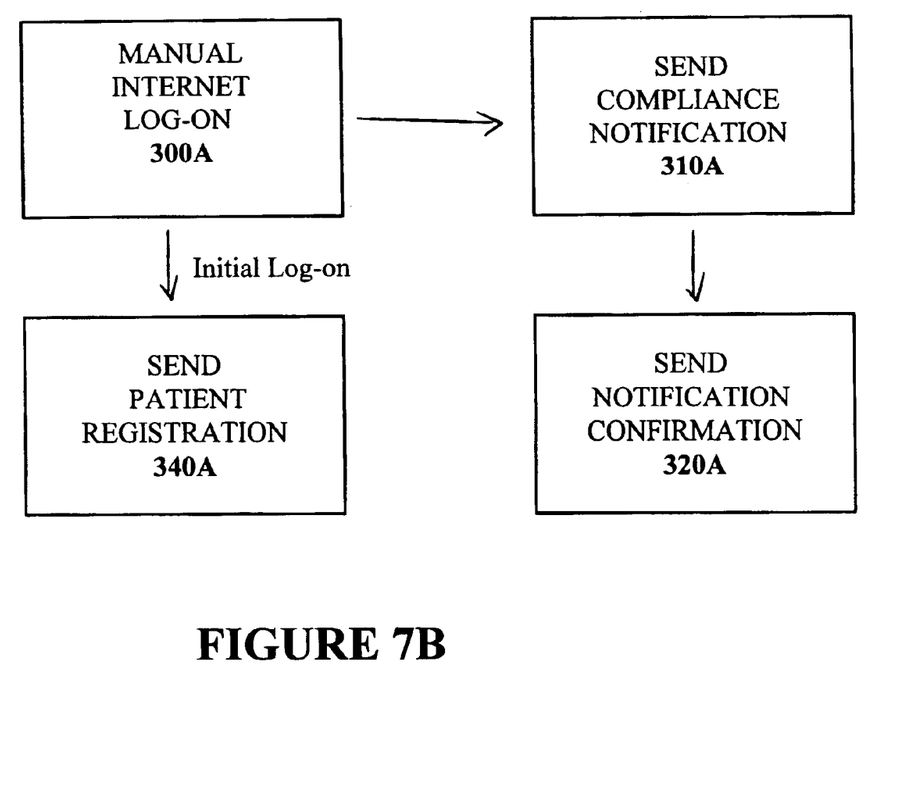
FIG. 7B is an operational flow chart illustrating a second embodiment of a compliance feature of the web-enabled medication dispensing system of the present invention.

FIG. 7B shows an operational flow chart for a user utilizing either the Internet-accessible or Internet-ready medication dispensing system and having selected a voluntary weekly compliance schedule. A manual log-on 300A to the Internet Service Provider is initiated by the patient/user. The controller transmits the Compliance Notification 310A, reporting the patient's compliance for the week. Optionally, once the Compliance Notification has been sent, a Notification Confirmation 320A can be displayed to advise the patient/user that the Notification was successfully transmitted. If a prior registration has not been transmitted to the ISP, the controller also transmits the Patient Registration 340A.

The web-enabled medication dispensing system of the present invention also provides an emergency assistance button 28/128, or touch-screen button 128*a*. When the system is linked to the Internet, the patient/user can touch or press emergency assistance button 28/128/128*a*, whereupon the controller will automatically log onto the ISP and transmit an emergency message. Alternatively, upon the activation of the emergency assistane button, the controller can be programmed to dial "911" directly over a telephone line, thus bypassing the Internet and allowing for rapid "911" response. The web-enabled medication dispensing system further may be equipped with a microphone 29/129, thereby providing the patient/user with voice communication with the "911" operator.

Figure 8:
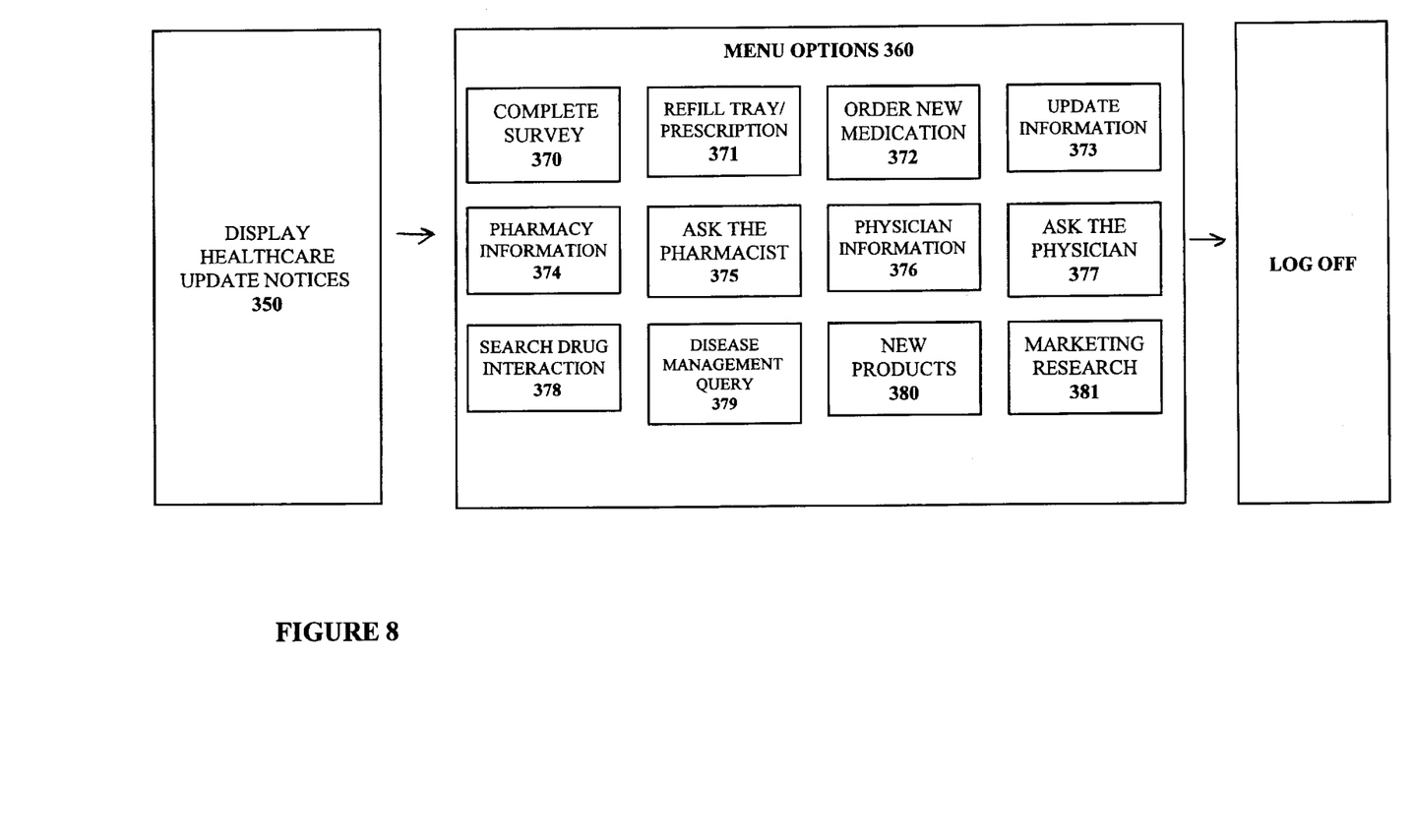
FIG. 8 is an flow chart illustrating the interactive Internet features of the web-enabled medication dispensing system of the present invention.

Once the patient registration has been transmitted, the web-enabled medication dispensing system of the present invention can access any of the designated databases and medical sites offered by the ISP any time the web-enabled medication dispensing system is connected to the ISP. Upon logging onto the ISP, one or more Healthcare Update Notices 350 may be displayed to the patient/user, as shown in FIG. 8. The content of the Healthcare Update Notices 350 is dependent on the Internet Server. Suitable content would include, for example, news relating to the user's medication, alternative or generic medications, reports related to the user's particular ailment or disease, announcements concerning healthcare products which may be of interest to the user, and the like.

Following the presentation of the Healthcare Update Notices 350, the user is presented with a menu of options 360. Although the particular options may be varied depending on the ISP, suitable options include for example, COMPLETE SURVEY 370, REFILL TRAY/PRESCRIPTION 371, ORDER NEW MEDICATION 372, UPDATE REGISTRATION INFORMATION 373, PHARMACY INFORMATION 374, ASK THE PHARMACIST 375, PHYSICIAN INFORMATION 376, ASK THE PHYSICIAN 377, SEARCH DRUG INTERACTION 378, DISEASE MANAGEMENT QUERY 379, NEW PRODUCTS 380, MARKETING RESEARCH 381.

Figure 9:
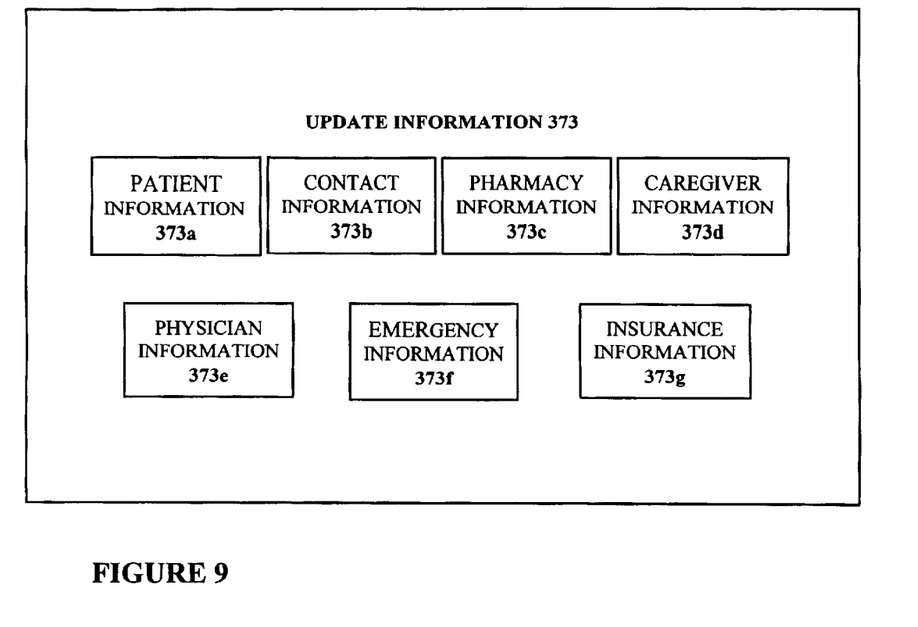
FIG. 9 is a flow chart illustrating a particular menu of options of the web-enabled medication dispensing system of the present invention.

Complete Survey 370 may be in the form of Yes/No questions simply requiring the patient/user to answer by touching the appropriate button on a touch-activated display screen, or may require the patient/user to enter information by means of a keyboard, such as keyboard 119/129. The patient/user can request that his/her prescription or pre-filled tray be re-filled and sent by selecting (e.g. by mouse-clicking or touch-activated clicking) REFILL TRAY/PRESCRIPTION 371 or may order a new prescription by selecting ORDER NEW PRESCRIPTION 372 and entering the name of the prescription. The patient/user also can update the registration information by selecting UPDATE REGISTRATION INFORMATION 373 and selecting from a menu of options as shown in FIG. 9, including for example, PATIENT 373*a*, CONTACT 373*b*, PHARMACY 373*c*, CAREGIVER 373*d*, PHYSICIAN 373*e*, EMERGENCY CONTACT 373*f* and INSURANCE 373*g*, and entering the new information, thus providing the ISP with current information. The patient/user can access a web-site or database provided by his/her specified pharmacy or physician by selecting PHARMACY INFORMATION 374 or PHYSICIAN INFORMATION 376, respectively, or can send an e-mail query by selecting ASK THE PHARMACIST 375 or ASK THE PHYSICIAN 377. The patient user also can access certain medical databases to research his/her medication regimen and related health issues by selecting SEARCH DRUG INTERACTION 378 or DISEASE MANAGEMENT QUERY 379. In addition, the patient can learn about new medical discoveries and innovations by selecting NEW PRODUCTS 380. The patient/user also may select MARKETING RESEARCH 381 to determine if he/she is a potential candidate for new medical supplies, medications and the like or wishes to participate in testing of new products.

While particular embodiments of the invention have been described, it will be understood, of course, that the invention is not limited thereto, and that many obvious modifications and variations can be made, and that such modifications and variations are intended to fall within the scope of the appended claims.

What is claimed is:

1. A medication dispensing system comprising:

(a) a base housing;

(b) a top housing connected to said base housing;

(c) a display screen secured to said top housing and electronically connected to said base housing and said top housing;

(d) a rotatable medication dispensing tray having a plurality of compartments removably disposed within said base housing, each of said plurality of compartments capable of holding at least one medication;

(e) a servo mechanism operatively connected to said rotatable medication dispensing tray;

(f) a microprocessor based controller electronically connected to said servo mechanism, said controller automatically rotates said medication dispensing tray to a dispensing position at a predetermined time, and (g) electronic communication means for connecting said medication dispensing system to the Internet.

2. The medication dispensing system in accordance with claim 1, wherein said top housing further comprises an access opening disposed therein which is configured to provide access to one of said plurality of compartments of said medication dispensing tray.

3. The medication dispensing system in accordance with claim 1, wherein said base housing further comprises a front panel having an opening therein of sufficient size for introducing and removing said medication dispensing tray.

4. The medication dispensing system in accordance with claim 1, wherein said top housing is hingedly connected to said base housing.

5. The medication dispensing system in accordance with claim 1, wherein when said controller rotates said dispensing tray at said predetermined time, said controller emits a signal indicating that said dispensing tray has been rotated.

6. The medication dispensing system in accordance with claim 5, further comprising an internal speaker, wherein said signal is an audible signal emitted by said internal speaker.

7. The medication dispensing system in accordance with claim 5, wherein said signal is a visual signal displayed on said display screen.

8. The medication dispensing system in accordance with claim 5, further comprising an internal speaker, wherein said signal is an audible signal emitted by said internal speaker, a visual signal displayed on said display screen or a combination thereof.

9. The medication dispensing system in accordance with claim 5, further comprising a response button electronically connected to said controller in such a manner that when said response button is actuated, said controller is instructed that said signal has been received.

10. The medication dispensing system in accordance with claim 1, further comprising an emergency assistance button electronically connected to said controller in such a manner that when said emergency assistance button is actuated, said controller is instructed to transmit an emergency message.

11. The medication dispensing system in accordance with claim 10, further comprising a telephone modem, wherein when said emergency assistance button is actuated, said controller is instructed to dial an emergency telephone number.

12. The medication dispensing system in accordance with claim 11, further comprising a microphone.

13. The medication dispensing system in accordance with claim 9, wherein said controller is programmable with a medication dispensing program which includes a data store comprising the predetermine time to rotate said dispensing tray and the name of said at least one medication.

14. The medication dispensing system in accordance with claim 13, wherein said data store further comprises the number of said plurality of compartments of said dispensing tray, patient data and a patient compliance schedule.

15. The medication dispensing system in accordance with claim 14, wherein said data store further comprises caregiver data and compliance notification data.

16. The medication dispensing system in accordance with claim 15, wherein said data store further comprises pharmacy data, physician data, insurance data and emergency contact data.

17. The medication dispensing system in accordance with claim 13, wherein said controller is programmable to connect to a predetermined Internet Service Provider in order to transmit said patient data and obtain a patient registration.

18. The medication dispensing system in accordance with claim 17, wherein said controller is programmable to connect to a predetermined Internet Service Provider to transmit said compliance schedule and compliance notification data.

19. The medication dispensing system in accordance with claim 18, wherein when said controller has been instructed that said signal has been received, said controller transmits a compliance notification to said Internet Service Provider.

20. The medication dispensing system in accordance with claim 18, wherein when said controller is not instructed within a predetermined time frame that a signal has been received, said controller transmits a non-compliance notification to said Internet Service Provider.

21. The medication dispensing system in accordance with claim 17, wherein said controller is programmable to transmit an order requesting a refill of said at least one medication or said dispensing tray containing said at least one medication when said medication dispensing system is connected to said pre-determined Internet Service Provider.

22. The medication dispensing system in accordance with claim 14, wherein said controller is programmable to update and transmit said patient data and said patient compliance schedule when said medication dispensing system is connected to said predetermined Internet Service Provider.

23. The medication dispensing system in accordance with claim 15, wherein said controller is programmable to update and transmit said caregiver data and compliance notification data when said medication dispensing system is connected to said predetermined Internet Service Provider.

24. The medication dispensing system in accordance with claim 16, wherein said controller is programmable to update and transmit said pharmacy data, physician data, insurance data and emergency contact data when said medication dispensing system is connected to said predetermined Internet Service Provider.

25. The medication dispensing system in accordance with claim 17, wherein said controller is programmable to receive Notices from said predetermined Internet Service Provider when said medication dispensing system is connected to said predetermined Internet Service Provider.

26. The medication dispensing system in accordance with claim 17, wherein said controller is programmable to access and search databases provided by said Internet Service Provider when said medication dispensing system is connected to said predetermined Internet Service Provider.

* * * * *